United States Patent [19]

Behl et al.

[11] Patent Number: 5,770,618
[45] Date of Patent: Jun. 23, 1998

[54] METHOD FOR INCREASING THE SOLUBILITY OF CLEMASTINE AND PHARMACEUTICAL COMPOSITIONS PREPARED THEREFROM

[75] Inventors: Charanjit R. Behl, Hauppauge; Jorge C. deMeireles, Syosset; Vincent D. Romeo, Massapequa Park; Anthony P. Sileno, Brookhaven Hamlet; Harish K. Pimplaskar, Lindenhurst; Wei J. Xia, Melville, all of N.Y.

[73] Assignee: Nastech Pharmaceutical Company, Inc., Hauppauge, N.Y.

[21] Appl. No.: 748,356

[22] Filed: Nov. 13, 1996

[51] Int. Cl.$^6$ .................................................. A61K 31/40
[52] U.S. Cl. ................................................ 514/408
[58] Field of Search ................................ 514/408

[56] References Cited

U.S. PATENT DOCUMENTS

| | | | |
|---|---|---|---|
| 4,232,002 | 11/1980 | Nogrady | 424/45 |
| 4,749,700 | 6/1988 | Wenig | 514/225.2 |
| 5,192,780 | 3/1993 | York et al. | 514/357 |

OTHER PUBLICATIONS

"Clemastine Fumarate", *American Hospital Formulary Service: Drug Information*, 16–17 (1996).
"Clemastine Fumarate", *American Hospital Formulary Service: Drug Information*, 15–16 (1994).
"Clemastine Fumarate", *Official Monographs of the United States Pharmacopeial Convention, Inc.*, 23, 385–386 (1995).
"Clemastine Fumarate", *Martindale: The Extra Pharmacopoeia*, 31, 438–439 (1996).
"Clemastine Fumarate", *Remington's Pharmaceutical Sciences*, 17, 1127 (1995).
USP DI, Drug Information for the Health Care Professtional, vol. 1, 13th ed., 1993.

*Primary Examiner*—Raymond Henley, III
*Attorney, Agent, or Firm*—Hoffmann & Baron, LLP

[57] ABSTRACT

A method is disclosed for increasing the solubility of clemastine through the use of organic acid or its salts as a solubilizing agent. Particularly useful as solubilizing agents are salts of carboxylic acids, such as fumarate, maleate and citrate. Pharmaceutical compositions containing clemastine, and organic acids or its salts as solubilizing agents, are also disclosed.

66 Claims, 1 Drawing Sheet

METHOD FOR INCREASING THE SOLUBILITY OF CLEMASTINE AND PHARMACEUTICAL COMPOSITIONS PREPARED THEREFROM

FIELD OF THE INVENTION

The present invention relates to a method for increasing the solubility of pharmaceutical agents, and compositions prepared therefrom, and more particularly to a method for increasing the solubility of clemastine, and compositions containing clemastine prepared therefrom.

BACKGROUND OF THE INVENTION

As is appreciated by those suffering from allergic rhinitis, antihistamines provide relief from its associated symptoms. One such antihistaminic agent that has become widely utilized is clemastine, and more particularly its salt, clemastine fumarate.

Typically, clemastine or its salts are administered orally to the subject, either in tablet form or as a syrup. Other routes of administering clemastine, or its salts, have not been utilized because liquid pharmaceutical compositions having a therapeutically effective amount of the agent have not been developed. The failure in developing such compositions is due to low solubility of clemastine, and its salts, in pharmaceutically acceptable solvents. For example, in Remington: The Science and Practice of Pharmacy, 19th edition, Volume II, 1995, clemastine fumarate is listed as being considered to be very slightly soluble in water, chloroform or ether, and only slightly soluble in alcohol.

Thus, there is a need in the art for a method of increasing the solubility of clemastine, and its salts, in pharmaceutically acceptable solvents. Similarly, there is a need in the art for liquid pharmaceutical compositions containing clemastine, and its salts, in therapeutically effective amounts.

It is an object of the present invention to provide a method of increasing the solubility of clemastine, especially its salts such as clemastine fumarate, in pharmaceutically acceptable solvents. It is also an object of the present invention to provide liquid pharmaceutical compositions that contain therapeutically effective amounts of clemastine, especially its salts such as clemastine fumarate.

SUMMARY OF THE INVENTION

The present invention provides a method for increasing the solubility of clemastine in a pharmaceutically acceptable solvent. This is accomplished by admixing in the solvent a solubilizing effective amount of an organic acid or its salt with the clemastine. Preferably, the clemastine added to the solvent is in an amount that provides a therapeutically effective concentration. The clemastine is also preferably in the form of a salt, such as clemastine fumarate. The solvent is preferably a polar solvent, in which water is most preferred. Alternatively, more than one solvent can also be utilized.

The organic acid or its salt is, preferably, a carboxylic acid or its salt. Preferred carboxylic acids includes fumaric acid, maleic acid, and citric acids. Preferred carboxylic acid salts include fumarate, maleate and citrate. Mixture of these solubilizing agents can also be utilized. The amount of the organic acid or its salt utilized is preferably an amount that provides the solution with concentration of at least about 0.01 molar (M), and more preferably at least about 0.1M, of the organic acid or its salt.

The present invention also provides liquid pharmaceutical compositions for administering clemastine to a mammal. The compositions includes a pharmaceutically acceptable solvent having a therapeutically effective amount of clemastine, and a solubilizing effective amount of an organic acid or its salt. Preferably, the clemastine is in the form of a salt, such as clemastine fumarate. The therapeutically effective amount of clemastine preferably is a clemastine concentration of at least 3 milligrams/milliliter (mg/mL), with about 5 mg/mL being more preferred. More preferably, the therapeutically effective amount of the clemastine is a clemastine concentration of at least about 6.7 mg/mL. The compositions can also include a buffer that maintains the compositions at a pH ranging from about 3 to about 10, and more preferably from about 4 to about 6. The compositions of the present invention are particularly suitable for the nasal administration of clemastine, and its salts, to a mammal.

Advantageously, as a result of the present invention, clemastine and its salts can now be solubilized in pharmaceutically acceptable solvents at concentrations previously unattainable. The ability to solubilize therapeutically effective amounts of clemastine in a solvent facilitates the utilization of drug delivery routes that previously could not effectively be utilized. Thus, the present invention also advantageously provides liquid pharmaceutical compositions having concentrations of clemastine in therapeutically effective amounts.

For a better understanding of the invention, reference is made to the following description and examples, the scope of which is pointed out in the appended claims.

BRIEF DESCRIPTION OF THE DRAWING

The FIGURE is a graph that depicts the solubilities of clemastine fumarate in aqueous salt solutions as a function of the organic acid salt concentration, after shaking for 24 hours at 25° C.

DETAILED DESCRIPTION OF THE INVENTION

Figure 1:
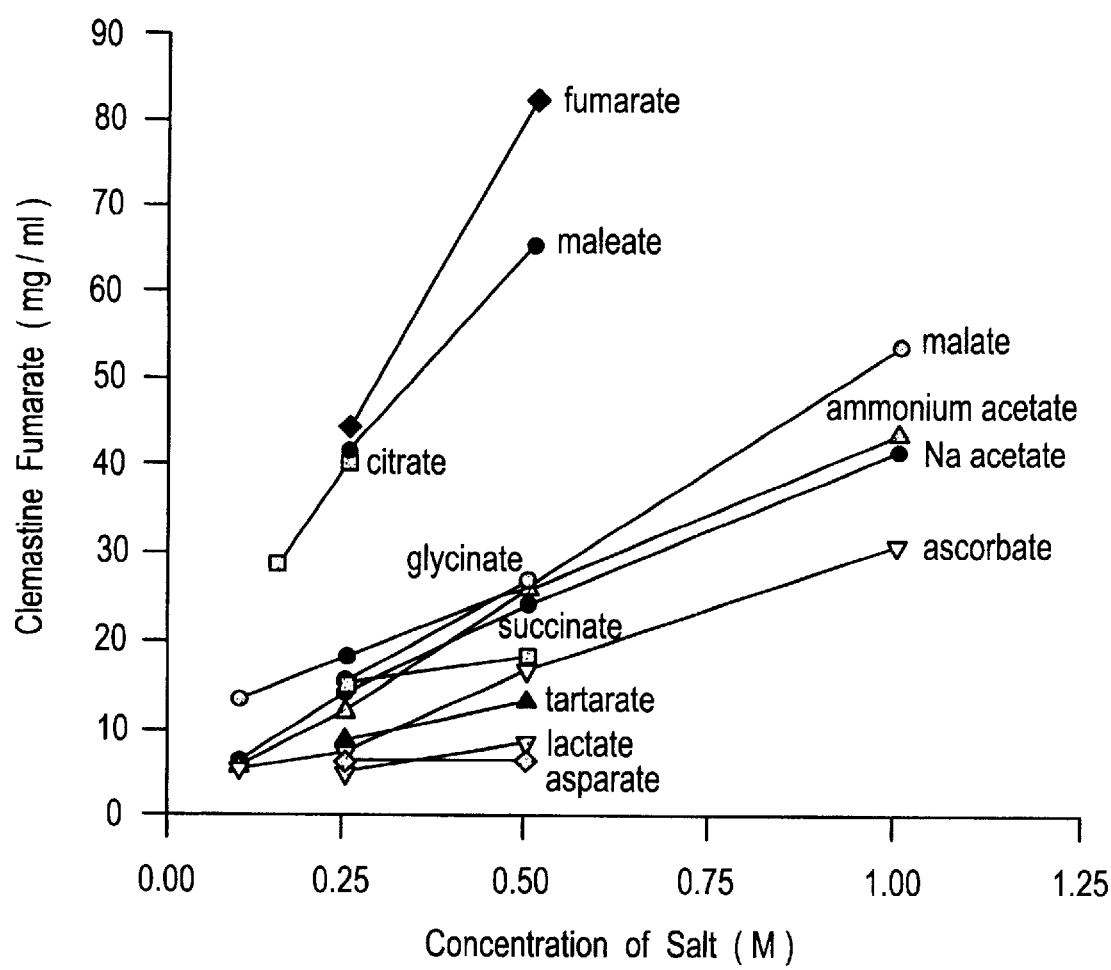

A method is provided for increasing the solubility of clemastine in pharmaceutically acceptable solvents. The method includes the step of admixing in the solvent a solubilizing effective amount of an organic acid or its salt, and the clemastine. It has been unexpectedly found that through the use of an organic acid or its salt, the solubility of clemastine in a pharmaceutically acceptable solvent is dramatically increased. As is well known in the art, clemastine and its salts are sparingly soluble in pharmaceutically acceptable solvents. This has, in turn, prevented the formulation of liquid pharmaceutical compositions containing therapeutically effective amounts of clemastine for administration via non-oral routes, e.g., intranasal and parenteral.

By reference to clemastine, reference is also made to the various salts of clemastine and, in particular, clemastine fumarate. The amount of clemastine to be utilized in the method of the present invention is preferably an amount that provides the resulting composition (i.e., solution) with a therapeutically effective concentration of the agent. A detailed description of the concentrations of clemastine suitable for the pharmaceutical compositions of the present invention will follow.

As previously described, a solubilizing effective amount of an organic acid or its salt is utilized to increase the solubility of clemastine in the solvent. By reference to a "solubilizing effective amount," reference is made to any amount of an organic acid or its salt utilized to increase the solubility of clemastine over the solubility exhibited by a control composition, at an equivalent pH, that does not contain the organic acid or its salt. Preferably, the solubilizing effective amount of the organic acid or its salt is an amount that provides the composition with a solubilizing agent concentration of at least about 0.01M, and more preferably of at least about 0.1M. The actual concentration of the organic acid or its salt utilized will vary with the amount of clemastine to be solubilized and with the selection of the organic acid or its salt as the solubilizing agent. However, to avoid possible adverse effects to the recipient of the pharmaceutical compositions of the present invention, the solubilizing agent concentration should preferably not exceed about 1.0M.

It is contemplated that any pharmaceutically acceptable organic acid or its salt can be utilized as the solubilizing agent in the present invention. A preferred class of such solubilizing agents is carboxylic acids or their salts. Carboxylic acid salts that can be utilized in accordance with the present invention include, but are not limited to, ammonium acetate, sodium acetate, sodium ascorbate, sodium citrate, sodium fumarate, sodium glycinate, sodium lactate, sodium malate, sodium maleate, sodium succinate and sodium tartarate. Of these carboxylic acid salts, citrate, maleate and fumarate are more preferred, with fumarate being most preferred. Combinations of these solubilizing agents can also be utilized.

In some circumstances, the desired organic acid salt may not be available in a USP grade. An alternative, therefore, is to utilize the acidic form of the salt in the preparation of the composition and subsequently adjust the pH of the composition to form the salt in situ. For example, in order to provide sodium maleate in situ, one can utilize maleic acid in the preparation of the composition and subsequently adjust the pH, e.g., with sodium hydroxide.

While not wishing to be bound by theory, it is believed that the organic acid or its salt ionically interacts with the clemastine to form a soluble entity in situ, which in turn dramatically increases the solubility of the clemastine. Such ionic interactions are considered weak and reversible.

Solvents to be utilized in accordance with the present invention include any solvent system, as long as it is pharmaceutically acceptable. The solvent preferably is a polar solvent, since it is believed that the polar nature of the solvent will facilitate the ionic interactions between the organic acid or its salt and the clemastine. Mixtures of solvents can also be utilized in accordance with the present invention. Preferred polar solvents include water and saline, in which water is most preferred.

As previously described, the organic acid or its salt and the clemastine are admixed in the solvent. The mixing of the components can be accomplished by any suitable means. Conventional means of dissolving the pharmaceutical components can be utilized. For example, the components can be stirred, sonicated, shaken, or vortexed. The amount of time necessary to facilitate a complete dissolution of the clemastine in the solvent will vary with the amount of clemastine utilized, the selected organic acid or its salt and the selected solvent. Typically, a time period of 24 hours is more than adequate to achieve a complete dissolution. These parameters can be easily determined by one skilled in the art.

The present invention also provides pharmaceutical compositions for administering clemastine to a mammal. The compositions include a pharmaceutically acceptable solvent having a therapeutically effective amount of the clemastine and a solubilizing effective amount of the organic acid or its salt.

The compositions of the present invention can be delivered to a mammal by a variety of administration routes. These include, but are not limited to, nasal, oral, sublingual, buccal, transdermal, rectal, ocular, intramuscular, intravenous, intraventricular, intrathecal and subcutaneous routes.

One preferred method of administering the pharmaceutical compositions of the present invention to a mammal is by nasal administration. Nasal administration is believed to avoid the so-called "first pass" effect, in which the orally administered clemastine is first circulated through the liver where a significant portion of the clemastine is metabolically inactivated. Thus, the nasal administration of clemastine may allow less clemastine to be utilized to achieve the same therapeutic effect as higher dosages via other administration routes.

The concentration of clemastine necessary to provide a therapeutically effective amount will vary by the route of drug administration, the frequency of dosing, the amount of clemastine delivered per dose, and the age and weight of the subject. As would be apparent to those skilled in the art, other factors may also affect the concentration of clemastine necessitated to provide a therapeutically effective amount. Typically, a clemastine concentration of at least 3 mg/mL or greater is utilized following the teaching of the present invention.

The pharmaceutical compositions for nasal administration preferably should contain an amount of clemastine effective for a bi-daily dosage protocol. Typically, about 0.1 mL of the composition is delivered into each nostril of the subject per dose. Thus to provide the subject with a therapeutically effective 1.0 mg of clemastine via a bi-daily dosage protocol, the pharmaceutical compositions for nasal application should contain a clemastine concentration of at least about 5 mg/mL. In the nasal application of clemastine fumarate, in which 1.34 mg of clemastine fumarate is the equivalent of 1.0 mg clemastine, the pharmaceutical compositions should contain a clemastine concentration of at least about 6.7 mg/mL. If a once daily dosage protocal is desired, the concentrations can be increased to 10 mg/mL or 13.4 mg/mL. However, following the teaching of the present invention, concentrations greater or less than those just described can easily be achieved by one skilled in the art.

Regardless of the method of administering clemastine, the pharmaceutical compositions preferably contain a buffer to maintain the pH of the composition. Any buffer system can be utilized with the present invention, as long as it is pharmaceutically acceptable. Examples of suitable buffers for the pharmaceutical compositions include, but are not limited to, acetate, citrate and phosphate buffers. Alternatively, the organic acid and its salt can be utilized as the buffer system to maintain the pH of the composition.

The pH of the pharmaceutical compositions can vary according to the route of administration. In the nasal application of the pharmaceutical compositions, the pH of the compositions preferably should be maintained from about 3 to about 10. Compositions having a pH less than 3, or greater than 10, can increase the risk of irritating the nasal mucosa of the recipient. Within this range, a pH from about 4 to about 6 is more preferred for the nasal compositions.

The viscosity of the compositions can be maintained at a desired level using a pharmaceutically acceptable thickening agent. One such preferred thickening agent is methyl cellulose because it is readily available and economical to utilize. Other suitable thickening agents include, but are not limited to, xanthan gum, carboxymethyl cellulose, hydroxypropyl cellulose, carbomer, and others. The concentration of the thickener agent will depend upon the agent selected and the viscosity desired. For example to administer the clemastine compositions of the present invention as a gel, a viscosity up to 15,000 centistokes per second (cps) can be utilized.

The pharmaceutical compositions of the present invention for nasal administration can also contain a humectant or a soothening/moisturizing agent to inhibit drying of the mucus membrane and to prevent irritation. A variety of pharmaceutically suitable humectants can be employed which include, but are not limited to, sorbitol, propylene glycol and glycerol. The concentration of the humectant or soothening/moisturizing agent(s) in the composition for nasal administration will also vary with agent selected.

In order to enhance absorption of the clemastine during nasal administration, one can also employ a therapeutically acceptable surfactant in the pharmaceutical composition. Surfactants that can be utilized with the present invention include, but are not limited to, polyoxyethylene derivatives of fatty acid partial esters of sorbitol anhydrides such as Tween 80, Polyoxyl 40 Stearate, Polyoxy ethylene 50 Stearate and Octoxynol. Generally, the surfactants to be utilized can be non-ionic, anionic, and cationic. These surfactants can be utilized in a concentration ranging from about 0.05 to about 10 percent. Absorption enhancers other than commonly known surfactants can also be utilized.

If desired, pharmaceutical excipients can also be used to localize the clemastine or its salts in the nostrils. These excipients can be drawn for bioadhesives and/or mucoadhesives and/or swelling/thickening agents.

The pharmaceutical compositions of the present invention can also employ a pharmaceutically acceptable preservative to increase product shelf life. Suitable preservatives that can be utilized include, but are not limited to, benzyl alcohol, parabens, thimerosal, chlorobutanol and benzalkonium chloride, with benzalkonium chloride being particularly preferred. Typically, the preservative is utilized in a concentration up to 2%. However, amounts greater than 2% can also be utilized if desired. The actual amount of preservative to be utilized can easily be ascertained by the skilled artisan.

EXAMPLES

The following non-limiting examples illustrate the invention in relation to solubilizing clemastine fumarate, as well as pharmaceutical compositions containing a therapeutically effective amounts of clemastine fumarate.

Example 1

Control compositions of clemastine fumarate in water at various pH values were prepared. Solutions of clemastine fumarate were formulated having final pH values of 3.9, 6.6 and 9.3 utilizing sodium hydroxide. The solution were prepared by shaking an excess amount of clemstine fumarate in water for 24 hours at 25° C., followed by filtration. The various concentrations of the clemastine fumarate in the filtrate were ascertained by UV spectroscopy. The solubilities of clemastine fumarate attained are shown in Table 1.

TABLE 1

Solubilities of Clemastine Fumarate, USP in Water

| Solvent System | Final pH | Clemastine Fumarate (mg/mL) |
|---|---|---|
| Water | 3.9 | less than 3 |
| Water + NaOH | 6.6 | less than 3 |
| Water + NaOH | 9.3 | less than 3 |

Example 2

In order to ascertain the effect of carboxylic acids or their salts as solubilizing agents for clemastine, various concentrations of the salts, ranging from 0.1M to 1M, were utilized. As in Example 1, the final concentration of clemastine fumarate in each solution was ascertained via UV spectroscopy. The various solubilities of clemastine fumarate achieved with the carboxylic acid salts, as a function of salt concentration, are shown in Table 2, and graphically depicted in the FIGURE.

TABLE 2

Solubilities of Clemastine Fumarate, USP, in Aqueous Salt Solutions Upon Shaking for 24 Hours at 25° C.

| Salt | Clemastine Furmarate Solubility, (mg/mL); Salt Concentrations in Molarity | | | | |
|---|---|---|---|---|---|
|  | 1.0 M | 0.5 M | 0.25 M | 0.15 M | 0.1 M |
| Ammonium Acetate | 43.3 pH: 5.7 | 25.7 pH: 5.6 | 12.2 pH: 5.5 | — | 6.1 pH: 5.4 |
| Sodium Acetate | 41.2 pH: 5.7 | 24.0 pH: 5.6 | 14.3 pH: 5.5 | — | 6.6 pH: 5.4 |
| Sodium Ascorbate | 30.6 pH: 5.3 | 16.7 pH: 5.2 | 7.5 pH: 5.2 | — | 5.5 pH: 5.2 |
| Sodium Citrate | * pH: 6.2 | * pH: 5.8 | 40.0 pH: 5.7 | 28.6 pH: 5.6 | — |
| Sodium Fumarate | — | 82.1 pH: 6.4 | 44.2 pH: 6.2 | — | — |
| Sodium Glycinate | — | 26.6 pH: 9.4 | 15.5 pH: 9.1 | — | — |
| Sodium Lactate | — | 8.6 pH: 5.1 | 5.0 pH: 5.0 | — | — |
| Sodium Malate | 29.3 pH: 5.7 | 25.5 pH: 5.5 | 16.9 pH: 6.0 | — | 13.8 pH: 54 |
| Sodium Maleate | 152.6 pH: 6.8 | 65.0 pH: 6.5 | 41.4 pH: 6.0 | — | — |
| Sodium Succinate | — | 18.2 pH: 6.3 | 15.4 pH: 6.1 | — | — |
| Sodium Tartarate | — | 13.3 pH: 5.1 | 9.0 pH: 5.1 | — | — |

*Solubility data is not available because of the formation of a liquid biphasic system.
**The pH values reported are for the filtrate solutions.

From Table 2 and the FIGURE, it is readily apparent that the carboxylic acid salts are effective as solubilizing agents for clemastine fumarate. For example, at a salt concentration of 0.25M, the concentration of clemastine fumarate in solution ranged from 5.04 mg/mL to 44.2 mg/mL. At a salt concentration of 0.5M, the concentration of clemastine fumarate in solution ranged from 8.59 mg/mL to 82.1 mg/mL. It is also readily apparent that the carboxylic acid salts of citrate, maleate and fumarate exhibited the greatest effect on solubilizing clemastine fumarate. In fact, the fumarate salt solution demonstrated the best results by exhibiting clemastine concentrations of 41.4 mg/mL at 0.25M and of 82.1 mg/mL at 0.5M. Among the salts tested a salt concentration of 1.0M, maleate provided a clemastine concentration of 152.6 mg/mL, which is a 50 fold improvement over the control solutions of Example 1. Thus, through the use of organic acids or their salts, concentrations of clemastine fumarate in pharmaceutically acceptable solvents are achieved that previously were unattainable.

Example 3

In order to ascertain the effects of pH in conjunction with the solubilizing agents of the present invention on the solubility of clemastine, clemastine fumarate was dissolved in various aqueous solutions buffered with a citrate salt and an acetate salt both at 0.5M. The final pH values of the solutions ranged from about 4 to about 6. The results of the buffer systems on the solubility of clemastine fumarate are shown in Table 3.

TABLE 3

Solubilities of Clemastine Fumarate, USP,
in Buffered Aqueous Solutions as a Function of pH

| Buffer System | pH Initial | pH Final | Clemastine Fumarate Solubility (mg/mL) |
|---|---|---|---|
| Citrate buffer, 0.5 M | 7.0 | 5.8 | 47.0 |
| Citrate buffer, 0.5 M | 6.5 | 5.6 | 46.3 |
| Citrate buffer, 0.5 M | 6.0 | 5.3 | 31.6 |
| Citrate buffer, 0.5 M | 5.0 | 4.9 | 3.3 |
| Citrate buffer, 0.5 M | 4.0 | 4.1 | 2.7 |
| Acetate buffer, 0.5 M | 6.7 | 5.7 | 24.0 |
| Acetate buffer, 0.5 M | 6.0 | 5.5 | 18.2 |
| Acetate buffer, 0.5 M | 5.5 | 5.3 | 11.2 |
| Acetate buffer, 0.5 M | 5.0 | 5.0 | 3.8 |
| Acetate buffer, 0.5 M | 4.0 | 4.1 | 0.6 |

The data listed in Table 3 demonstrates that buffer systems utilizing organic acid salts can also dramatically increase the solubility of clemastine fumarate. In Example 1, the clemastine fumarate concentrations attained in the non-buffered control compositions were all less than 3 mg/mL. At a pH value of 7.0/5.8, the citrate buffered solution resulted in a clemastine fumarate concentration of 47.0 mg/mL. Similarly, the acetate buffered solution at a pH of 6.7/5.7 resulted in a clemastine fumarate concentration of 24.0 mg/mL. Thus, the solubility of the clemastine at various pH values was dramatically enhanced through the use of the carboxylic acids and their salts. As a result, one skilled in the art can easily prepare various formulations having clemastine concentrations of 3 mg/mL or greater by varying the combination of the type of the organic acid or its salt, the concentration of the solubilizing agent and the pH of the mixture.

Example 4

A pharmaceutical composition particularly useful for nasally administering clemastine to a mammal was prepared in the following manner. Approximately 0.6 g of Monopotassium Phosphate, USP, was dissolved in 90 mL of Purified Water, USP. Approximately 0.8 g of Disodium Phosphate, USP, was thereafter added and stirred to dissolution. After which approximately 3.0 g of Glycine, USP, (i.e., the solubilizing agent) was added and stirred to dissolution. This was followed by the addition of 0.01 g of Edetate Disodium Dihydrate, USP. Approximately 0.04 g of a 50% Benzalkonium Chloride Solution, NF, was added to the solution and stirred to dissolution. Subsequently, approximately 2.0 g of a 96 wt. % solution of Glycerin, USP, was added to the solution and also stirred to dissolution. Finally, Clemastine Fumarate, USP, in an amount of 2.07 g was added to the solution and stirred to dissolution. The pH of the solution was adjusted with 1.0N solutions of NaOH or HCL. The volume of the solution was then adjusted to a total volume of 100 mL with Purified Water, USP. Thereafter, the solution was filtered through a one micrometer filter and stored in a Type I glass bottle.

The resulting composition exhibited a pH of 6.4±0.3, and an organic salt concentration of 0.01M. The composition contained a therapeutically effective 6.7 mg/mL of clemastine fumarate. A summary of the components utilized to prepare the composition is shown in Table 4.

TABLE 4

| Components | Amts. (g/100 mL) |
|---|---|
| Clemastine Fumarate, USP | 0.67 |
| Glycine, USP | 3.00 |
| Monopotassium Phosphate, USP | 0.60 |
| Disodium Phosphate, USP | 0.80 |
| Edetate Disodium Dihydrate, USP | 0.01 |
| Benzalkonium Chloride (50% Solution), NF | 0.04 |
| Glycerin (96%), USP | 2.00 |
| NaOH/HCl (1.0 N), USP | To adjust pH |
| Purified Water, USP | q.s. 100 mL |
| Total Volume | 100 mL |

Example 5

A pharmaceutical composition of clemastine fumarate was prepared in accordance with Example 4, utilizing fumaric acid as the solubilizing agent. The resulting composition exhibited a pH of 6.4±0.3, and an organic acid salt concentration of 0.11M. The composition contained a therapeutically effective 6.7 mg/mL of clemastine fumarate. The summary of the components utilized to prepare the composition is shown in Table 5.

TABLE 5

| Components | Amts. (g/100 mL) |
|---|---|
| Clemastine Fumarate, USP | 0.67 |
| Fumaric Acid, NF | 1.16 |
| Sodium Hydroxide, NF | 0.80 |
| Monopotassium Phosphate, USP | 0.65 |
| Disodium Phosphate, USP | 0.75 |
| Edetate Disodium Dihydrate, USP | 0.01 |
| Benzalkonium Chloride (50% solution), NF | 0.04 |
| Glycerin (96%), USP | 2.00 |
| NaOH/HCl (1.0 N), USP | To adjust pH |
| Purified Water, USP | q.s. to 100 mL |
| Total Volume | 100 mL |

Example 6

A pharmaceutical composition of clemastine fumarate was prepared in accordance with Example 4, utilizing maleic acid as the solubilizing agent. The resulting composition exhibited a pH of 6.4±0.03 and an organic acid salt concentration of 0.11M. The composition contained a therapeutically effective 6.7 mg/mL of clemastine fumarate. A summary of the components utilized to prepare the composition is shown in Table 6.

TABLE 6

| Components | Amts. (g/100 mL) |
| --- | --- |
| Clemastine Fumarate, USP | 0.67 |
| Maleic Acid, NF | 1.16 |
| Sodium Hydroxide, NF | 0.80 |
| Monopotassium Phosphate, USP | 0.85 |
| Disodium Phosphate, USP | 0.55 |
| Edetate Disodium Salt, USP | 0.01 |
| Benzalkonium Chloride (50% solution), NF | 0.04 |
| Glycerin, USP (96%) | 2.00 |
| NaOH/HCl (1.0 N), USP | To adjust pH |
| Purified Water, USP | q.s. to 100 mL |
| Total Volume | 100 mL |

Example 7

A pharmaceutical composition of clemastine fumarate was prepared in accordance with Example 4, utilizing maleic acid as the solubilizing agent. The resulting composition exhibited a pH of 6.0 at ±0.5, and an organic acid salt concentration of 0.11M. The composition contained a therapeutically effective 6.7 mg/mL of clemastine fumarate. A summary of the components utilized to prepare the composition is shown in Table 7.

TABLE 7

| Components | Amts. (g/100 mL) |
| --- | --- |
| Clemastine Fumarate, USP | 0.67 |
| Maleic Acid, NF | 1.34 |
| Sodium Hydroxide, NF | 0.80 |
| Disodium Phosphate, USP | 0.85 |
| Edetate Disodium Salt, USP | 0.55 |
| Benzalkonium Chloride (50% solution.), NF | 0.01 |
| Glycerin (96%), USP | 2.00 |
| NaOH/HCl (1.0 N), USP | To adjust pH |
| Purified Water, USP | q.s. to 100 mL |
| Total Volume | 100 mL |

Example 8

A pharmaceutical composition of clemastine fumarate was prepared in accordance with Example 4, utilizing citric acid as the solubilizing agent. The resulting composition had a pH of 6.4±0.3 and an organic salt concentration of approximately 0.1M. A summary of the components utilized to prepare the pharmaceutical composition is shown in Table 8.

TABLE 8

| Components | Amts. (g/100 mL) |
| --- | --- |
| Clemastine Fumarate, USP | 0.67 |
| Citric Acid, Anhydrous, USP | 1.02 |
| Sodium Hydroxide, NF | 0.70 |
| Edetate Disodium Salt, USP | 0.01 |
| Benzalkonium Chloride (50% solution), NF | 0.04 |
| Glycerin (96%), USP | 2.00 |
| NaOH/HCl (1.0 N), USP | To adjust pH |
| Purified Water, USP | q.s. to 100 mL |
| Total Volume | 100 mL |

While the invention has been described as to what are presently believed to be the preferred embodiments of the invention, those skilled in the art will realize the various changes and modifications which can be made to the invention without departing from the spirit of such invention. All such changes and modifications will fall within the scope of the present invention and are therefore intended to be claimed.

We claim:

1. A pharmaceutical composition for administering clemastine or its pharmaceutically acceptable salt to a mammal, which comprises a pharmaceutically acceptable solvent having dissolved therein a therapeutically effective amount of said clemastine and a solubilizing effective amount of an organic acid or its salt, wherein said solubilizing effective amount provides the solution with a concentration of at least about 0.1M of said organic acid or said salt.

2. A composition of claim 1, wherein said clemastine is clemastine fumarate.

3. A composition of claim 1, wherein said solvent is a polar solvent.

4. A composition of claim 3, wherein said polar solvent is selected from the group consisting of water, saline and a mixture thereof.

5. A composition of claim 1, wherein said solvent is a mixture of pharmaceutically acceptable solvents.

6. A composition of claim 1, wherein said organic acid or its salt is a carboxylic acid or its salt.

7. A composition of claim 5, wherein said carboxylic acid salt is selected from to the group consisting of fumarate, maleate, citrate and mixtures thereof.

8. A composition of claim 5, wherein said carboxylic acid is selected from the group consisting of fumaric acid, maleic acid, citric acid and mixture thereof.

9. A composition of claim 1, wherein said therapeutically effective amount of said clemastine is a clemastine concentration of at least 3 mg/mL.

10. A composition of claim 9, wherein said therapeutically effective amount of said clemastine is a clemastine concentration of at least about 5 mg/mL.

11. A composition of claim 10, wherein said therapeutically effective amount of said clemastine is a clemastine concentration of at least about 6.7 mg/mL.

12. A composition of claim 11, wherein said therapeutically effective amount of said clemastine is a clemastine concentration of at least 13.4 mg/mL.

13. A composition of claim 1, further comprising a buffer to maintain said composition at a pH from about 3 to about 10.

14. A composition of claim 13, wherein said buffer maintains said composition at a pH from about 4 to about 6.

15. A pharmaceutical composition for administering clemastine or its pharmaceutically acceptable salt to a mammal, which comprises a pharmaceutically acceptable solvent having dissolved therein a therapeutically effective amount of said clemastine, and a solubilizing effective amount of an organic acid or its salt as the sole solubilizing agent, wherein said therapeutically effective amount of said clemastine is a clemastine concentration of at least 3 mg/mL.

16. A composition of claim 15, wherein said clemastine is clemastine fumarate.

17. A composition of claim 15, wherein said solvent is a polar solvent.

18. A composition of claim 17, wherein said polar solvent is selected from the group consisting of water, saline and a mixture thereof.

19. A composition of claim 15, wherein said solvent is a mixture of pharmaceutically acceptable solvents.

20. A composition of claim 15, wherein said organic acid or its salt is a carboxylic acid or its salt.

21. A composition of claim 20, wherein said carboxylic acid salt is selected from to the group consisting of fumarate, maleate, citrate and mixtures thereof.

22. A composition of claim 20, wherein said carboxylic acid is selected from the group consisting of fumaric acid, maleic acid, citric acid and mixture thereof.

23. A composition of claim 15, wherein said therapeutically effective amount of said clemastine is a clemastine concentration of at least about 5 mg/mL.

24. A composition of claim 23, wherein said therapeutically effective amount of said clemastine is a clemastine concentration of at least about 6.7 mg/mL.

25. A composition of claim 24, wherein said therapeutically effective amount of said clemastine is a clemastine concentration of at least 13.4 mg/mL.

26. A composition of claim 15, further comprising a buffer to maintain said composition at a pH from about 3 to about 10.

27. A composition of claim 26, wherein said buffer maintains said composition at a pH from about 4 to about 6.

28. A pharmaceutical composition for administering clemastine or its pharmaceutically acceptable salt to a mammal, which consists essentially of a pharmaceutically acceptable solvent having dissolved therein a therapeutically effective amount of said clemastine, and a solubilizing effective amount of an organic acid or its salt as the sole solubilizing agent, wherein said therapeutically effective amount of said clemastine is a clemastine concentration of at least 3 mg/mL.

29. A composition of claim 28, wherein said clemastine is clemastine fumarate.

30. A composition of claim 28, wherein said solvent is a polar solvent.

31. A composition of claim 30, wherein said polar solvent is selected from the group consisting of water, saline and a mixture thereof.

32. A composition of claim 28, wherein said solvent is a mixture of pharmaceutically acceptable solvents.

33. A composition of claim 28, wherein said organic acid or its salt is a carboxylic acid or its salt.

34. A composition of claim 33, wherein said carboxylic acid salt is selected from to the group consisting of fumarate, maleate, citrate and mixtures thereof.

35. A composition of claim 33, wherein said carboxylic acid is selected from the group consisting of fumaric acid, maleic acid, citric acid and mixture thereof.

36. A composition of claim 28, wherein said therapeutically effective amount of said clemastine is a clemastine concentration of at least about 5 mg/mL.

37. A composition of claim 36, wherein said therapeutically effective amount of said clemastine is a clemastine concentration of at least about 6.7 mg/mL.

38. A composition of claim 37, wherein said therapeutically effective amount of said clemastine is a clemastine concentration of at least 13.4 mg/mL.

39. A composition of claim 28, further comprising a buffer to maintain said composition at a pH from about 3 to about 10.

40. A composition of claim 39, wherein said buffer maintains said composition at a pH from about 4 to about 6.

41. A method for increasing the solubility of clemastine or its pharmaceutically acceptable salt in a pharmaceutically acceptable solvent, comprising the step of admixing, in said solvent, a solubilizing effective amount of an organic acid or its salt and said clemastine, wherein said solubilizing effective amount provides the solution with a concentration of at least about 0.1M of said organic acid or said salt.

42. A method of claim 41, wherein said clemastine is clemastine fumarate.

43. A method of claim 41, wherein said solvent is a polar solvent.

44. A method of claim 42, wherein said polar solvent is selected from the group consisting of water, saline and a mixture thereof.

45. A method of claim 41, wherein said organic acid or its salt is a carboxylic acid or its salt.

46. A method of claim 45, wherein said carboxylic acid salt is selected from the group consisting of fumarate, maleate, citrate and mixtures thereof.

47. A method of claim 45, wherein said carboxylic acid is selected from the group consisting of fumaric acid, maleic acid, citric acid and mixtures thereof.

48. A method of claim 41, wherein said clemastine is admixed in an amount that provides the solution with a therapeutically effective amount.

49. A method for increasing the solubility of clemastine or its pharmaceutically acceptable salt in a pharmaceutically acceptable solvent, comprising the step of admixing, in said solvent, a solubilizing effective amount of an organic acid or its salt as the sole solubilizing agent and said clemastine in an amount that provides a clemastine concentration of at least 3 mg/mL.

50. A method of claim 49, wherein said clemastine is clemastine fumarate.

51. A method of claim 49, wherein said solvent is a polar solvent.

52. A method of claim 51, wherein said polar solvent is selected from the group consisting of water, saline and a mixture thereof.

53. A method of claim 49, wherein said organic acid or its salt is a carboxylic acid or its salt.

54. A method of claim 53, wherein said carboxylic acid salt is selected from the group consisting of fumarate, maleate, citrate and mixtures thereof.

55. A method of claim 53, wherein said carboxylic acid is selected from the group consisting of fumaric acid, maleic acid, citric acid and mixtures thereof.

56. A method of claim 49, wherein said solubilizing effective amount of said organic acid or its salt is an amount that provides the solution with a concentration of at least about 0.01M of said organic acid or said salt.

57. A method of claim 56, wherein said solubilizing effective amount is an amount that provides the solution with a concentration of at least about 0.1M of said organic acid or said salt.

58. A method for increasing the solubility of clemastine or its pharmaceutically acceptable salt in a pharmaceutically acceptable solvent, consisting essentially of the step of admixing, in said solvent, a solubilizing effective amount of an organic acid or its salt as the sole solubilizing agent and said clemastine in an amount that provides a clemastine concentration of at least 3 mg/mL.

59. A method of claim 58, wherein said clemastine is clemastine fumarate.

60. A method of claim 58, wherein said solvent is a polar solvent.

61. A method of claim 60, wherein said polar solvent is selected from the group consisting of water, saline and a mixture thereof.

62. A method of claim 58, wherein said organic acid or its salt is a carboxylic acid or its salt.

63. A method of claim 62, wherein said carboxylic acid salt is selected from the group consisting of fumarate, maleate, citrate and mixtures thereof.

64. A method of claim 62, wherein said carboxylic acid is selected from the group consisting of fumaric acid, maleic acid, citric acid and mixtures thereof.

65. A method of claim 58, wherein said solubilizing effective amount of said organic acid or its salt is an amount that provides the solution with a concentration of at least about 0.01M of said organic acid or said salt.

66. A method of claim 65, wherein said solubilizing effective amount is an amount that provides the solution with a concentration of at least about 0.1M of said organic acid or said salt.

\* \* \* \* \*